US011919884B2

(12) United States Patent
Huang et al.

(10) Patent No.: US 11,919,884 B2
(45) Date of Patent: Mar. 5, 2024

(54) METHOD FOR PREPARING VORICONAZOLE L-CAMPHORSULPHONATE AND VORICONAZOLE

(71) Applicant: Zhejiang Huahai Pharmaceutical Co., Ltd., Zhejiang (CN)

(72) Inventors: Hu Huang, Zhejiang (CN); Wenfeng Huang, Zhejiang (CN); Guoliang Tu, Zhejiang (CN); Zhongming Xu, Zhejiang (CN); Qianghui Wu, Zhejiang (CN); Zhaoyang Meng, Zhejiang (CN); Yuling Fang, Zhejiang (CN)

(73) Assignee: Zhejiang Huahai Pharmaceutical Co., Ltd., Zhejiang (CN)

( * ) Notice: Subject to any disclaimer, the term of this patent is extended or adjusted under 35 U.S.C. 154(b) by 1175 days.

(21) Appl. No.: 16/330,692

(22) PCT Filed: Nov. 10, 2016

(86) PCT No.: PCT/CN2016/105312
§ 371 (c)(1),
(2) Date: Mar. 5, 2019

(87) PCT Pub. No.: WO2018/045629
PCT Pub. Date: Mar. 15, 2018

(65) Prior Publication Data
US 2021/0276980 A1    Sep. 9, 2021

(30) Foreign Application Priority Data

Sep. 8, 2016 (CN) .......................... 201610811521.4

(51) Int. Cl.
| C07D 403/06 | (2006.01) |
| C07B 57/00 | (2006.01) |
| C07C 303/22 | (2006.01) |
| C07C 309/19 | (2006.01) |

(52) U.S. Cl.
CPC ........ *C07D 403/06* (2013.01); *C07B 2200/13* (2013.01)

(58) Field of Classification Search
CPC .............. C07D 403/06; C07B 2200/13; C07B 2200/07; C07B 57/00; C07C 2603/66; C07C 303/22; C07C 309/19
See application file for complete search history.

(56) References Cited

U.S. PATENT DOCUMENTS 6,586,594 B1    7/2003    Butters et al.

FOREIGN PATENT DOCUMENTS

| CN | 1473825 A | 2/2004 |
| CN | 101765595 A | 6/2010 |
| CN | 102516233 A | 6/2012 |
| CN | 102807563 A | 12/2012 |
| CN | 104884450 A | 9/2015 |
| CN | 105503834 A | 4/2016 |
| WO | WO 2007/013096 A1 | 2/2007 |
| WO | WO 2007/132354 A2 | 11/2007 |
| WO | WO 2008/075205 A2 | 6/2008 |
| WO | WO 2009/084029 A2 | 7/2009 |
| WO | WO 2010/095145 A1 | 8/2010 |
| WO | WO 2014/060900 A1 | 4/2014 |

OTHER PUBLICATIONS

Extended European Search Report and Search Opinion dated Jul. 5, 2019 in connection with EP Application No. 16915563.7.
International Search Report and Written Opinion dated Jun. 15, 2017 in connection with PCT/CN2016/105312.

*Primary Examiner* — Sun Jae Yoo
(74) *Attorney, Agent, or Firm* — Wolf, Greenfield & Sacks, P.C.

(57) ABSTRACT

A method for preparing voriconazole L-camphorsulphonate and voriconazole. The method for preparing voriconazole L-camphorsulphonate comprises: method 1: dissolving (2R, 3S)/(2S,3R) isomer mixture and L-camphor sulphonic acid in water and acetone, and performing crystallisation filtration to obtain voriconazole L-camphorsulphonate; method 2: (a) dissolving a mixture of isomer mixture and L-camphor sulphonic acid in a first solvent and then performing crystallisation filtration; or (a') dissolving L-camphorsulphonate of the isomer mixture in a first solvent and then performing crystallisation filtration; (b) concentrating the filtrate obtained in step (a) or (a') into a solid; and (c) dissolving the solid obtained in step (b) in a second solvent and performing crystallisation filtration to obtain voriconazole L-camphorsulphonate. Adjusting the resolution solvent effectively reduces production costs and facilitates recycling of the resolution solvent.

19 Claims, No Drawings

METHOD FOR PREPARING VORICONAZOLE L-CAMPHORSULPHONATE AND VORICONAZOLE

CROSS-REFERENCE TO RELATED APPLICATIONS

This application is the National Phase Under 35 U.S.C. § 371 of PCT International Application No. PCT/CN2016/105312, filed Nov. 10, 2016, which claims the priority of the Chinese Patent Application No. 201610811521.4, with the title of "METHOD FOR PREPARING VORICONAZOLE RESOLUTION INTERMEDIATE", filed on Sep. 8, 2016 before the China National Intellectual Property Administration, which applications are incorporated herein by reference in their entirety

TECHNICAL FIELD

The present invention relates to a method for preparing voriconazole L-camphorsulfonate and voriconazole.

BACKGROUND OF THE INVENTION

Voriconazole (VRC, UK109496) is a novel antifungal drug synthesized on the basis of fluconazole by Pfizer of the United States, and it is mainly used for patients with progressive and fatal immune damage. The market prospect is broad, because voriconazole has a wide-spectrum antifungal activity, strong antifungal effect, good safety, and the demand for antifungal drugs in the domestic market is growing rapidly.

The chemical name of voriconazole is: (2R,3S)-2-(2,4-difluorophenyl)-3-(5-fluoropyrimidin-4-yl)-1-(1H-1,2,4-triazol-1-yl)-2-butanol, the structural formula thereof is as shown in formula I:

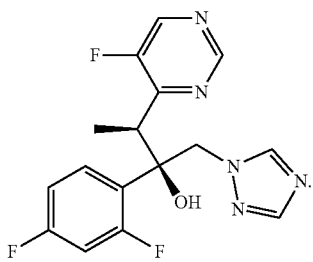

I

The racemate of voriconazole is an important intermediate, its chemical name is: (2R,3S/2S,3R)-2-(2,4-difluorophenyl)-3-(5-fluoropyrimidin-4-yl)-1-(1H-1,2,4-triazol-1-yl)-2-butanol, the structural formula thereof is as shown in formula II:

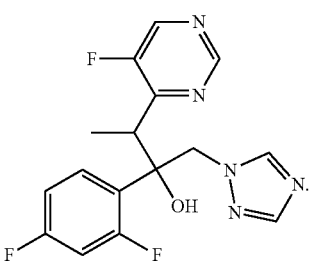

II

The racemate of voriconazole needs to be resolved in one step to obtain voriconazole, i.e., (2R, 3S)-2-(2,4-difluorophenyl)-3-(5-fluoropyrimidin-4-yl)-1-(1H-1,2,4-triazol-1-yl)-2-butanol. There are generally two methods for the resolution of isomers. The first one is a chiral induction during the reaction. This method generally requires the use of a chiral catalyst, rendering a relatively high cost and adverse to large-scale industrial production. The second one is to adopt chiral resolving agents for resolution. The chiral resolving agents can be relatively simply recovered and can be used repeatedly. This method is often used in industrial production.

Patent EP2444398 A2 discloses a method for resolving the racemate of voriconazole by using a chiral resolving agent. The resolving agent used is L-camphorsulfonic acid, and the resolution solvent is a mixed solvent of methanol and acetone. The reaction route is as follows:

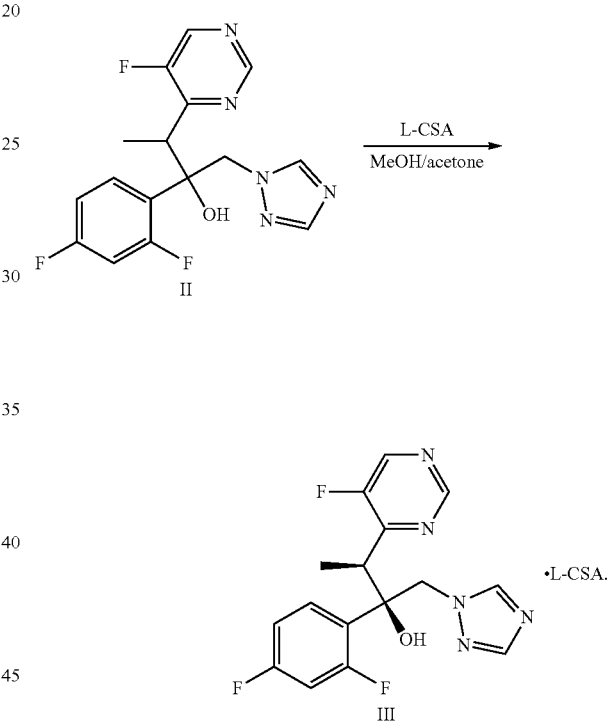

The above resolving method has the following problems:
1. The two solvents (methanol and acetone) have similar boiling points and relatively high volatility, so it is difficult to separate two solvents. Therefore, the recovery of the solvents is a serious problem. The use of the current solvents also increases production cost. At the same time, it does not meet the requirements of environmentally friendly production;
2. In the process of resolution, the amount of resolution solvent is very large, and the production capacity is low, which seriously affects the large-scale production of the resolved voriconazole;
3. There are still a large amount of the compound as shown in formula III and the isomer L-camphorsulfonate of (2S,3R)-2-(2,4-difluorophenyl)-3-(5-fluoropyrimidin-4-yl)-1-(1H-1,2,4-triazol-1-yl)-2-butanol represented by the following formula IV remaining in the resolving mother liquor:

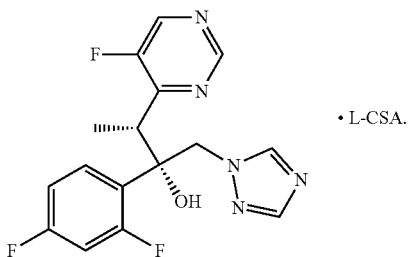

SUMMARY OF THE INVENTION

In order to solve the above problems, an aspect of the present invention provides a method for preparing voriconazole L-camphorsulfonate, comprising the following steps:

Method 1: dissolving a mixture of (2R,3S)/(2S,3R)-2-(2,4-difluorophenyl)-3-(5-fluoropyrimidin-4-yl)-1-(1H-1,2,4-triazol-1-yl)-2-butanol and L-camphorsulfonic acid in a mixed solvent of water and acetone, cooling and crystallizing, and filtering to obtain a crystal of voriconazole L-camphorsulfonate;

Method 2: (a) dissolving a mixture of (2R,3S)/(2 S,3R)-2-(2,4-difluorophenyl)-3-(5-fluoropyrimidin-4-yl)-1-(1H-1,2,4-triazol-1-yl)-2-butanol and L-camphorsulfonic acid in a first solvent, crystallizing, and filtering to remove a crystal enriched with L-camphorsulfonate of (2S,3R)-2-(2,4-difluorophenyl)-3-(5-fluoropyrimidin-4-yl)-1-(1H-1,2,4-triazol-1-yl)-2-butanol; or (a') dissolving a mixture of L-camphorsulfonate of (2R, 3S)/(2 S, 3R)-2-(2,4-difluorophenyl)-3-(5-fluoropyrimidin-4-yl)-1-(1H-1,2,4-triazol-1-yl)-2-butanol in a first solvent, crystallizing, and filtering to remove a crystal enriched with L-camphorsulfonate of (2 S, 3R)-2-(2,4-difluorophenyl)-3-(5-fluoropyrimidin-4-yl)-1-(1H-1,2,4-triazol-1-yl)-2-butanol;

(b) concentrating a filtrate obtained in step (a) or (a') to dryness to obtain a solid; and (c) dissolving the solid obtained in step (b) in a second solvent and crystallizing to obtain L-camphorsulfonate of (2R,3S)-2-(2,4-difluorophenyl)-3-(5-fluoropyrimidin-4-yl)-1-(1H-1,2,4-triazol-1-yl)-2-butanol.

In the method 1 of the present invention, a resolving solvent different from that of the prior art is used, which can reduce the amount of solvent, reduce production cost, improve productivity, thereby having a great value for industrial production.

Compared to the prior art which directly combines voriconazole in a mixture with a resolving agent, and then crystallizing and separating, the method 2 of the present invention uses a completely different method: firstly crystallizing and removing isomer of (2S,3R)-2-(2,4-difluorophenyl)-3-(5-fluoropyrimidin-4-yl)-1-(1H-1,2,4-triazol-1-yl)-2-butanol, concentrating filtrate to obtain a mixture of (2R,3S)/(2 S,3R)-2-(2,4-difluorophenyl)-3-(5-fluoropyrimidin-4-yl)-1-(1H-(1,2,4-triazol-1-yl)-2-butanol, redissolving and crystallizing the mixture to obtain L-camphorsulfonate of (2R,3S)-2-(2,4-difluorophenyl)-3-(5-fluoropyrimidin-4-yl)-1-(1H-1,2,4-triazol-1-yl)-2-butanol.

Among them, the two isomers in the mixture of (2R, 3S)/(2 S,3R)-2-(2,4-difluorophenyl)-3-(5-fluoropyrimidin-4-yl)-1-(1H-1,2,4-triazol-1-yl)-2-butanol in the method 1 may exist in any ratio, for example, a ratio of voriconazole to its isomer may be 99:1 to 40:60. In one embodiment, this ratio can be 1:1.

Among them, the two isomers in the mixture of (2R, 3S)/(2 S,3R)-2-(2,4-difluorophenyl)-3-(5-fluoropyrimidin-4-yl)-1-(1H-1,2,4-triazol-1-yl)-2-butanol in the method 2 may exist in any ratio, for example, a ratio of voriconazole to its isomer may be 50:50 to 1:99.

In the above methods 1 and 2, preferably, a ratio of the mixture of (2R,3S)/(2S,3R)-2-(2,4-difluorophenyl)-3-(5-fluoropyrimidin-4-yl)-1-(1H-1,2,4-triazol-1-yl)-2-butanol to L-camphorsulfonic acid is, for example, 1:1 to 1:1.5.

The method 2 of the present invention is highly suitable for using in, for example, the recovery of mother liquor after the resolution of the racemate of voriconazole in the method 1, which is very beneficial for increasing the overall yield of the resolution and reducing the cost.

In the above methods of the present invention, the second solvent used in step (c) of the method 2 is not particularly limited, it may be referred to the solvent such as a mixed solvent of acetone and methanol used in the method for resolving the racemate of voriconazole reported in the prior art, or a mixed solvent of acetone and water provided by the present invention. In one embodiment, the second solvent is a mixed solvent of acetone and water.

In the above methods, the first solvent is selected from the group consisting of a mixture of a $C_4$-$C_8$ ketone solvent and water, isopropanol or ethanol. The amount of the first solvent is not particularly limited, as long as the mixture can be completely dissolved therein to obtain a clarified solution.

In the above method, a volume ratio of the $C_4$-$C_8$ ketone solvent to water is 100:1 to 1:100, preferably 50:1 to 5:1, more preferably 25:1 to 10:1.

The $C_4$-$C_8$ ketone solvent is preferably butanone, methyl isobutyl ketone or methyl butanone.

The crystallization in step (a) or (a') may be performed at a temperature of 0 to 40° C., preferably 15° C. to 25° C.

A volume ratio of acetone to water may be 100:1 to 1:100, preferably 15:1 to 5:1.

Acetone and water in the method 1 or the second solvent in the method 2 may be in an amount of 10 mL/g to 30 mL/g, preferably 10 mL/g to 15 mL/g, with respect to the mixture of (2R,3S)/(2S,3R)-2-(2,4-difluorophenyl)-3-(5-fluoropyrimidin-4-yl)-1-(1H-1,2,4-triazol-1-yl)-2-butanol.

The crystallization in the method 1 or in step (c) of the method 2 may be performed at a temperature of 0° C. to 40° C., preferably 15° C. to 30° C.

Another aspect of the present invention also provides a method of preparing voriconazole, comprising adding voriconazole L-camphorsulfonate prepared according to the methods described above with a base to obtain voriconazole.

A further aspect of the present invention provides a crystal enriched with L-camphorsulfonate of (2 S,3R)-2-(2,4-difluorophenyl)-3-(5-fluoropyrimidin-4-yl)-1-(1H-1,2,4-triazol-1-yl)-2-butanol, wherein a ratio of L-camphorsulfonate of (2 S,3R)-2-(2,4-difluorophenyl)-3-(5-fluoropyrimidin-4-yl)-1-(1H-1,2,4-triazol-1-yl)-2-butanol to L-camphorsulfonate of (2R,3S)-2-(2,4-difluorophenyl)-3-(5-fluoropyrimidin-4-yl)-1-(1H-1,2,4-triazol-1-yl)-2-butanol in the crystal is greater than 1, preferably greater than 5, and further preferably L-camphorsulfonate of (2 S,3R)-2-(2,4-difluorophenyl)-3-(5-fluoropyrimidin-4-yl)-1-(1H-1,2,4-triazol-1-yl)-2-butanol in the crystal has a purity greater than 90%, preferably greater than 98%.

DETAILED DESCRIPTION OF THE INVENTION

Example 1

Method 1 was used for resolution in this example. The racemate of voriconazole (15 g), L-camphorsulfonic acid (10 g), acetone (150 mL) and water (15 mL) were mixed, and warmed to 50° C. so that the solid was completely dissolved to give a clarified solution. Then the solution was naturally cooled down to 20° C., stirred for 2 h at 20° C., and filtered to obtain a solid crystal; wherein the compound of formula III had an ee % of 99.7% and a yield of 40.4%.

Example 2

Method 1 was used for resolution in this example. The racemate of voriconazole (9 g), L-camphorsulfonic acid (6 g), acetone (150 mL) and water (30 mL) were mixed, and warmed to 50° C. so that the solid was completely dissolved to give a clarified solution. Then the solution was naturally cooled down to 0° C., stirred for 2 h at 0° C., and filtered to obtain a solid crystal; wherein the compound of formula III had an ee % of 99.3% and a yield of 30.1%.

Example 3

Method 1 was used for resolution in this example. The racemate of voriconazole (9 g), L-camphorsulfonic acid (6 g), acetone (150 mL) and water (15 mL) were mixed, and warmed to 50° C. so that the solid was completely dissolved to give a clarified solution. Then the solution was naturally cooled down to 25° C., stirred for 2 h at 25° C., and filtered to obtain a solid crystal; wherein the compound of formula III had an ee % of 99.7% and a yield of 36.6%.

Example 4

Method 1 was used for resolution in this example. The racemate of voriconazole (15 g), L-camphorsulfonic acid (10 g), acetone (150 mL) and water (10 mL) were mixed, and warmed to 50° C. so that the solid was completely dissolved to give a clarified solution. Then the solution was naturally cooled down to 25° C., stirred for 2 h at 25° C., and filtered to obtain a solid crystal; wherein the compound of formula III had an ee % of 99.8% and a yield of 37.5%.

Example 5

Method 2 was used for resolution in this example.

A resolving mother liquor obtained repeatedly by the method according to Example 1 was concentrated to give a solid (100 g, wherein a ratio of the compound of formula III to the compound of formula IV=18:82); the solid was added into a flask, together with butanone (300 mL) and water (15 mL), warmed to 50° C. and stirred for 30 min, then cooled down to 25° C. and stirred for 2 h, and then filtered to remove solid crystal (this crystal comprises the compound of formula IV in a purity of 99.27%). The filtrate was concentrated to dryness to give a solid (34.2 g, wherein a ratio of the compound of formula III to the compound of formula IV=55:45).

The concentrated solid was added into a flask, together with acetone (205.2 mL) and water (20.5 mL), warmed to 50° C., stirred to give a clarified solution. Then the solution was slowly cooled down to 25° C., and stirred at 25° C. for 2 h, and filtered. Then the filter cake was eluted with a mixed solution of acetone/water (V/V 10:1, 33 mL) once, and filtered to obtain a solid, wherein the compound of formula III had an ee % of 99.6% and a yield of 12.1%. The yield of the accumulated compound of formula III obtained with the method of Example 1 was 47.6%.

Example 6

Method 2 was used for resolution in this example.

The racemate of voriconazole (30 g), L-camphorsulfonic acid (200 g), butanone (150 mL) and water (7.5 mL) were mixed, and warmed to 50° C. till the solution was clarified. Then the solution was naturally cooled down to 25° C., stirred for 2 h at 25° C., and filtered to remove solid (this solid comprises the compound of formula IV in a purity of 98.9%). The filtrate was concentrated to give a solid (34.2 g, wherein a ratio of the compound of formula III to the compound of formula IV=70:30).

The concentrated solid was added into a flask, together with acetone (205.2 mL) and water (20.5 mL), warmed to 50° C., stirred at 50° C. for 1 h, then slowly cooled down to 25° C., and stirred at 25° C. for 2 h, and then filtered. Then the filter cake was eluted with a mixed solution of acetone/water (V/V 10:1, 33 mL) once and dried to obtain a solid of 18.5 g, wherein the compound of formula III had an ee % of 99.4% and a yield of 37%.

Examples 7-11

The effects of different solvent systems on the collection of isomers enriched with formula IV were investigated. The results obtained are shown in the following table:

| Number | Experiment procedure | compound of formula III:compound of formula IV |
|---|---|---|
| Example 7 | The racemate of voriconazole (10 g), L-camphorsulfonic acid (3.3 g), and isopropanol (110 g) were heated to 70° C. to reflux to give a clarified solution, and then the solution was naturally cooled to 15° C., crystallized and filtered to give a solid. | 16.2:83.8 |
| Example 8 | The racemate of voriconazole (15 g), L-camphorsulfonic acid (6.6 g), and ethanol (110 g) were heated to 60° C. to reflux to give a clarified solution, and then the solution was naturally cooled to 15° C., crystallized and filtered to give a solid. | 15.7:84.3 |

-continued

| Number | Experiment procedure | compound of formula III:compound of formula IV |
|---|---|---|
| Example 9 | The racemate of voriconazole (12 g), L-camphorsulfonic acid (8.0 g), and methylisobutylketone (120 mL) were heated to 50° C. to reflux to give a clarified solution, and then the solution was naturally cooled to 20° C., crystallized and filtered to give a solid. | 1.46:98.54 |
| Example 10 | The racemate of voriconazole (15 g), L-camphorsulfonic acid (10 g), butanone (150 mL) and water (15 mL) were heated to 50° C. to reflux to give a clarified solution, and then the solution was naturally cooled to 20° C., crystallized and filtered to give a solid. | 1.02:98.96 |
| Example 11 | The racemate of voriconazole (15 g), L-camphorsulfonic acid (10 g), methylbutanone (150 mL) and water (15 mL) were heated to 50° C. to reflux to give a clarified solution, and then the solution was naturally cooled to 20° C., crystallized and filtered to give a solid. | 1.92:98.08 |

Comparative Example

The racemate of voriconazole (15.1 g) was dissolved in acetone (288 mL), and a solution of L-camphorsulfonic acid (8.51 g) in methanol (96 mL) was added, the mixture was heated to 50° C., to give a clarified solution. Then the solution was slowly cooled to 20° C., and stirred at 20° C. for 18 hours, filtered and detected by HPLC. The voriconazole L-camphorsulfonate had an ee % of 99.8%, and a yield of 35%.

As can be seen from the above comparative example, the solvent system of acetone and methanol is used in a relatively large amount of about 24.5 ml/g, and the minimum amount can reach to 10 ml/g in the method of the present invention; while the two solvents (alcohol and acetone) used in the comparative example have similar boiling points and relatively high volatility, making separation difficult, so that using the method in the comparative example greatly increases the production cost.

The above is only the preferred embodiment of the present invention, and is not intended to limit the present invention. Any modifications, equivalent substitutions, improvements, etc., which are made within the spirit and principles of the present invention, should be included within the protection scope of the present invention.

The invention claimed is:

1. A method for preparing voriconazole L-camphorsulfonate, comprising:
   Method 1: dissolving a mixture of (2R,3S)/(2S,3R)-2-(2,4-difluorophenyl)-3-(5-fluoropyrimidin-4-yl)-1-(1H-1,2,4-triazol-1-yl)-2-butanol and L-camphorsulfonic acid in a mixed solvent of water and acetone, cooling and crystallizing, and filtering to obtain a crystal of voriconazole L-camphorsulfonate; or
   Method 2: (a) dissolving a mixture of (2R,3S)/(2S,3R)-2-(2,4-difluorophenyl)-3-(5-fluoropyrimidin-4-yl)-1-(1H-1,2,4-triazol-1-yl)-2-butanol and L-camphorsulfonic acid in a first solvent, crystallizing, and filtering to remove a crystal enriched with L-camphorsulfonate of (2S, 3R)-2-(2,4-difluorophenyl)-3-(5-fluoropyrimidin-4-yl)-1-(1H-1,2,4-triazol-1-yl)-2-butanol; or
   (a') dissolving a mixture of L-camphorsulfonate of (2R, 3S)/(2S,3R)-2-(2,4-difluorophenyl)-3-(5-fluoropyrimidin-4-yl)-1-(1H-1,2,4-triazol-1-yl)-2-butanol in a first solvent, crystallizing, and filtering to remove a crystal enriched with L-camphorsulfonate of (2S,3R)-2-(2,4-difluorophenyl)-3-(5-fluoropyrimidin-4-yl)-1-(1H-1,2,4-triazol-1-yl)-2-butanol;
   (b) concentrating a filtrate obtained in step (a) or (a') to dryness to obtain a solid; and
   (c) dissolving the solid obtained in step (b) in a second solvent and crystallizing to obtain L-camphorsulfonate of (2R,3S)-2-(2,4-difluorophenyl)-3-(5-fluoropyrimidin-4-yl)-1-(1H-1,2,4-triazol-1-yl)-2-butanol.

2. The method according to claim 1, wherein the first solvent is selected from the group consisting of a mixture of $C_4$-$C_8$ ketone solvent and water, isopropanol and ethanol.

3. The method according to claim 1, wherein the second solvent is selected from the group consisting of a mixed solvent of acetone and water, or a mixed solvent of methanol and acetone.

4. The method according to claim 2, wherein a volume ratio of the $C_4$-$C_8$ ketone solvent to water is 100:1 to 1:100.

5. The method according to claim 2, wherein the $C_4$-$C_8$ ketone solvent is butanone, methyl isobutyl ketone or methyl butanone.

6. The method according to claim 5, wherein a temperature of crystallization in step (a) or (a') is 0° C. to 40° C.

7. The method according to claim 1, wherein a volume ratio of acetone to water is 100:1 to 1:100.

8. The method according to claim 1, wherein acetone and water in the method 1 or the second solvent in the method 2 is used in an amount of 10 mL/g to 30 mL/g, with respect to the mixture of (2R,3S)/(2S,3R)-2-(2,4-difluorophenyl)-3-(5-fluoropyrimidin-4-yl)-1-(1H-1,2,4-triazol-1-yl)-2-butanol.

9. The method according to claim 1, wherein a temperature of crystallization in the method 1 or in step (c) of the method 2 is 0° C. to 40° C.

10. The method according to claim 1, wherein in the crystal enriched with L-camphorsulfonate of (2S,3R)-2-(2,4-difluorophenyl)-3-(5-fluoropyrimidin-4-yl)-1-(1H-1,2,4-triazol-1-yl)-2-butanol, in step (a) and step (a') of the method 2, a ratio of L-camphorsulfonate of (2S,3R)-2-(2,4-difluorophenyl)-3-(5-fluoropyrimidin-4-yl)-1-(1H-1,2,4-triazol-1-yl)-2-butanol to L-camphorsulfonate of (2R,3S)-2-(2,4-difluorophenyl)-3-(5-fluoropyrimidin-4-yl)-1-(1H-1,2,4-triazol-1-yl)-2-butanol is greater than 1.

11. The method according to claim 4, wherein the volume ratio of the $C_4$-$C_8$ ketone solvent to water is 50:1 to 5:1.

12. The method according to claim 4, wherein the volume ratio of the $C_4$-$C_8$ ketone solvent to water is 25:1 to 10:1.

13. The method according to claim 6, wherein the temperature of crystallization in step (a) or (a') is 15° C. to 25° C.

14. The method according to claim 7, wherein the volume ratio of acetone to water is 15:1 to 5:1.

15. The method according to claim 8, wherein acetone and water in the method 1 or the second solvent in the method 2 is used in an amount of 10 mL/g to 15 mL/g, with respect to the mixture of (2R,3S)-2-(2,4-difluorophenyl)-3-(5-fluoropyrimidin-4-yl)-1-(1H-1,2,4-triazol-1-yl)-2-butanol and (2S,3R)-2-(2,4-difluorophenyl)-3-(5-fluoropyrimidin-4-yl)-1-(1H-1,2,4-triazol-1-yl)-2-butanol.

16. The method according to claim 9, wherein the temperature of crystallization in the method 1 or in step (c) of the method 2 is 15° C. to 30° C.

17. The method according to claim 10, wherein the ratio of L-camphorsulfonate of (2S,3R)-2-(2,4-difluorophenyl)-3-(5-fluoropyrimidin-4-yl)-1-(1H-1,2,4-triazol-1-yl)-2-butanol to L-camphorsulfonate of (2R,3S)-2-(2,4-difluorophenyl)-3-(5-fluoropyrimidin-4-yl)-1-(1H-1,2,4-triazol-1-yl)-2-butanol is greater than 5.

18. The method according to claim 10, wherein the L-camphorsulfonate of (2S,3R)-2-(2,4-difluorophenyl)-3-(5-fluoropyrimidin-4-yl)-1-(1H-1,2,4-triazol-1-yl)-2-butanol in the crystal has a purity greater than 90%.

19. The method according to claim 10, wherein the L-camphorsulfonate of (2S,3R)-2-(2,4-difluorophenyl)-3-(5-fluoropyrimidin-4-yl)-1-(1H-1,2,4-triazol-1-yl)-2-butanol in the crystal has a purity greater than 98%.

* * * * *